(12) United States Patent
Ternes et al.

(10) Patent No.: US 9,079,032 B2
(45) Date of Patent: Jul. 14, 2015

(54) POWER SUPPLY MANAGEMENT FOR IMPLANTABLE NEUROSTIMULATION DEVICES

(71) Applicant: Cardiac Pacemakers, Inc., St. Paul, MN (US)

(72) Inventors: David J. Ternes, Roseville, MN (US); Scott Vanderlinde, Plymouth, MN (US); Ramprasad Vijayagopal, Shoreview, MN (US); Scot C. Boon, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 250 days.

(21) Appl. No.: 13/663,003

(22) Filed: Oct. 29, 2012

(65) Prior Publication Data

US 2013/0073008 A1     Mar. 21, 2013

Related U.S. Application Data

(63) Continuation-in-part of application No. 13/274,448, filed on Oct. 17, 2011, now Pat. No. 8,792,992.

(60) Provisional application No. 61/412,114, filed on Nov. 10, 2010.

(51) Int. Cl.
    *A61N 1/36*      (2006.01)

(52) U.S. Cl.
    CPC ........ *A61N 1/36153* (2013.01); *A61N 1/36135* (2013.01); *A61N 1/36157* (2013.01)

(58) Field of Classification Search
    CPC ........... A61N 1/36153; A61N 1/36157; A61N 1/36135; A61N 1/378; A61N 1/36139; A61N 1/36521

USPC .......................................... 607/8, 28, 62, 63
See application file for complete search history.

(56) References Cited

U.S. PATENT DOCUMENTS

| 4,354,498 A | 10/1982 | Weigert et al. |
| 4,363,324 A | 12/1982 | Kusserow |

(Continued)

OTHER PUBLICATIONS

US 7,684,855, 3/2010, Giftakis, et al. (withdrawn).

(Continued)

*Primary Examiner* — Michael Kahelin
*Assistant Examiner* — Mallika D Fairchild
(74) *Attorney, Agent, or Firm* — Schwegman Lundberg & Woessner, P.A.

(57) ABSTRACT

An apparatus comprises a therapy circuit that provides a neural stimulation current, an impedance measurement circuit that measures a value of impedance at the output of the therapy circuit, a supply voltage generating circuit that provides an adjustable supply voltage value to the therapy circuit including a first supply voltage value when in a first mode, and a control circuit communicatively coupled to the therapy circuit, the impedance measuring circuit, and the supply voltage generating circuit. The control circuit, upon receiving an indication to exit the first mode, initiates an impedance measurement by the impedance measurement circuit, determines the second supply voltage value using the impedance measurement, and initiates a change from the first supply voltage value to the second supply voltage value. The second supply voltage value is sufficient to operate the therapy circuit and to provide a specified load current value to the measured impedance.

20 Claims, 12 Drawing Sheets

(56) References Cited

U.S. PATENT DOCUMENTS

| | | |
|---|---|---|
| 5,540,724 A | 7/1996 | Cox |
| 5,690,683 A | 11/1997 | Haefner et al. |
| 5,836,983 A | 11/1998 | Weijand et al. |
| 6,317,628 B1 | 11/2001 | Linder et al. |
| 6,721,600 B2 * | 4/2004 | Jorgenson et al. ............. 607/27 |
| 7,216,000 B2 | 5/2007 | Sieracki et al. |
| 7,389,147 B2 | 6/2008 | Wahlstrand et al. |
| 7,493,161 B2 | 2/2009 | Libbus et al. |
| 7,881,782 B2 | 2/2011 | Libbus et al. |
| 8,036,739 B2 | 10/2011 | Ternes |
| 8,792,992 B2 | 7/2014 | Linder et al. |
| 2002/0068957 A1 * | 6/2002 | Wolfe et al. ..................... 607/2 |
| 2005/0283197 A1 | 12/2005 | Daum et al. |
| 2006/0095080 A1 | 5/2006 | Libbus et al. |
| 2006/0271118 A1 | 11/2006 | Libbus et al. |
| 2009/0156957 A1 | 6/2009 | Linder et al. |
| 2009/0157132 A1 | 6/2009 | Linder et al. |
| 2010/0010553 A1 | 1/2010 | Libbus et al. |
| 2010/0298897 A1 | 11/2010 | Chavan et al. |
| 2011/0224747 A1 | 9/2011 | Maile et al. |
| 2012/0116482 A1 | 5/2012 | Linder et al. |

OTHER PUBLICATIONS

"U.S. Appl. No. 13/274,448, Response filed Jun. 27, 2013 to Non Final Office Action mailed Apr. 24, 2013", 10 pgs.

"U.S. Appl. No. 13/274,448, Response filed Dec. 11, 2013 to Non Final Office Action mailed Oct. 2, 2013", 9 pgs.

"U.S. Appl. No. 13/274,448, Non Final Office Action mailed Apr. 24, 2013", 10 pgs.

"U.S. Appl. No. 13/274,448, Non Final Office Action mailed Oct. 2, 2013", 12 pgs.

"U.S. Appl. No. 13/274,448, Notice of Allowance mailed Mar. 17, 2014", 5 pgs.

Foutz, T. J., et al., "Energy Efficient Neural Stimulation: Coupling Circuit Design and Membrane Biophysics", PLOS One, www.plosone.org; vol. 7, Issue 12, e51901, (Dec. 2012), 1-8.

* cited by examiner

POWER SUPPLY MANAGEMENT FOR IMPLANTABLE NEUROSTIMULATION DEVICES

PRIORITY CLAIM

This application is a continuation-in-part of U.S. patent application Ser. No. 13/274,448, filed on Oct. 17, 2011, which claims the benefit of U.S. Provisional Patent Application Ser. No. 61/412,114, filed on Nov. 10, 2010, both of which are incorporated herein by reference in their entireties.

BACKGROUND

Ambulatory medical devices can be wearable or implantable. Implantable medical devices (IMDs) include, among other things, cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural or neuro-stimulation capability. CFM devices typically use pacing output circuits dedicated to provide output voltage pulses, while neural stimulation devices typically use output circuits dedicated to provide constant current or constant current pulses.

OVERVIEW

This document discusses examples of techniques for generating and delivering neural stimulation therapy. In particular, it relates to devices and methods to provide delivery of quasi-constant current therapy and to manage the supply voltage used to deliver neural stimulation therapy.

An apparatus example includes a therapy circuit configured to provide a neural stimulation current at an output of the therapy circuit, an impedance measurement circuit configured to measure a value of impedance at the output of the therapy circuit, a supply voltage generating circuit configured to provide an adjustable supply voltage value to the therapy circuit including a first supply voltage value when in a first mode, and a control circuit communicatively coupled to the therapy circuit, the impedance measuring circuit, and the supply voltage generating circuit. The control circuit, upon receiving an indication to exit the first mode, is configured to: initiate an impedance measurement by the impedance measurement circuit, determine the second supply voltage value using the impedance measurement, wherein the second supply voltage value is sufficient to operate the therapy circuit and to provide a specified load current value to the measured impedance, and initiate a change from the first supply voltage value to the second supply voltage value.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A medical device may include one or more of the features, structures, methods, or combinations thereof described herein. For example, a cardiac stimulator may be implemented to include one or more of the advantageous features or processes described below. It is intended that such a monitor, stimulator, or other implantable, partially implantable, ambulatory, or wearable device need not include all of the features described herein, but may be implemented to include selected features that provide for unique structures or functionality. Such a device may be implemented to provide a variety of therapeutic or diagnostic functions.

Figure 1:
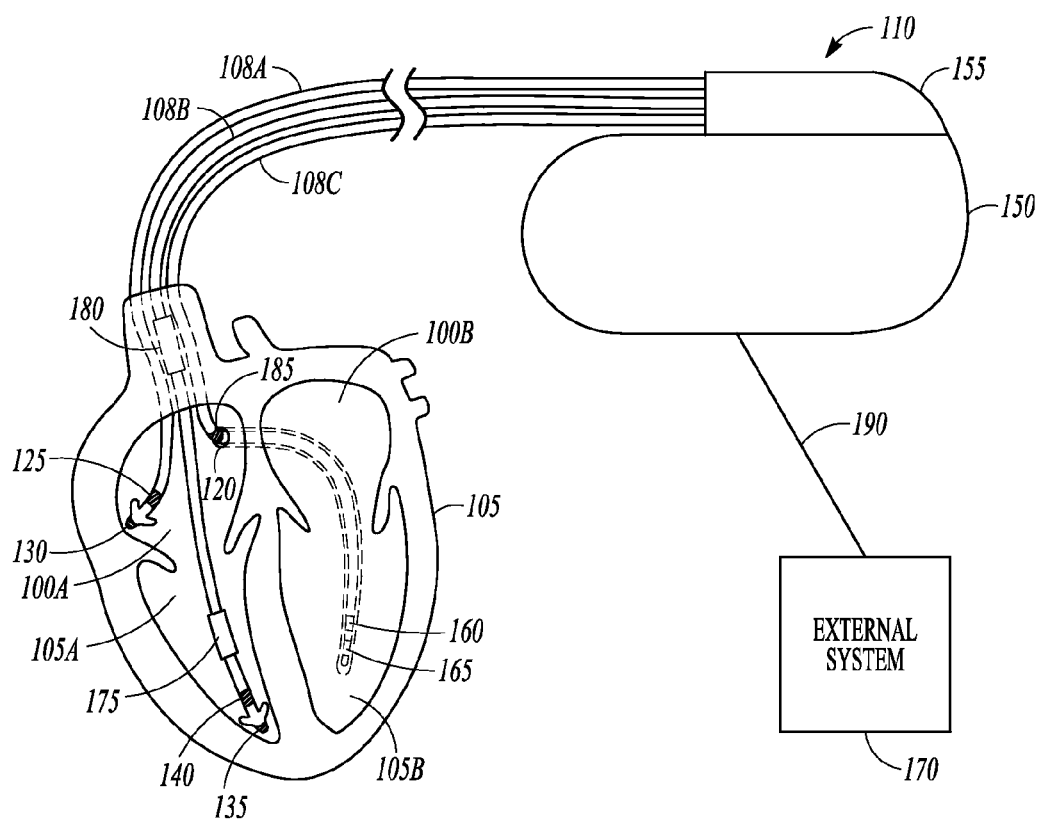
FIG. 1 is an illustration of an example of portions of a system that includes an implantable medical device.

This document discusses devices and methods for generating and delivering neural stimulation therapy. An ambulatory medical device includes medical devices that can be worn, implanted, or partially implanted. FIG. 1 is an illustration of portions of a system 100 that uses an implantable medical device (IMD) 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 182.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110. Electrode configurations can include a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

An IMD that delivers neural stimulation therapy can include leads and electrodes designed for placement to provide therapy to specific areas of the nervous system, including the sympathetic nervous system and the parasympathetic nervous system. The sympathetic nervous system is associated with increased blood flow, heart rate, and increased skeletal muscle blood flow. The parasympathetic nervous system is associated with decreased blood pressure, heart rate, and increased digestion.

Stimulating the sympathetic and parasympathetic nervous systems can affect other areas besides heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

In some examples, a neural stimulation device may locally stimulate specific nerve endings in arterial walls rather than stimulate afferent nerve trunks in an effort to stimulate a desired response (e.g. reduced hypertension) while reducing the undesired effects of indiscriminate stimulation of the nervous system. In certain examples, baroreceptor sites in the pulmonary artery are stimulated. In some examples, a neural stimulation device stimulates baroreceptor sites or nerve endings in the aorta and the chambers of the heart, and/or an afferent nerve trunk, such as the vagus, carotid and aortic nerves. In some examples, neural stimulation devices stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figure 2:
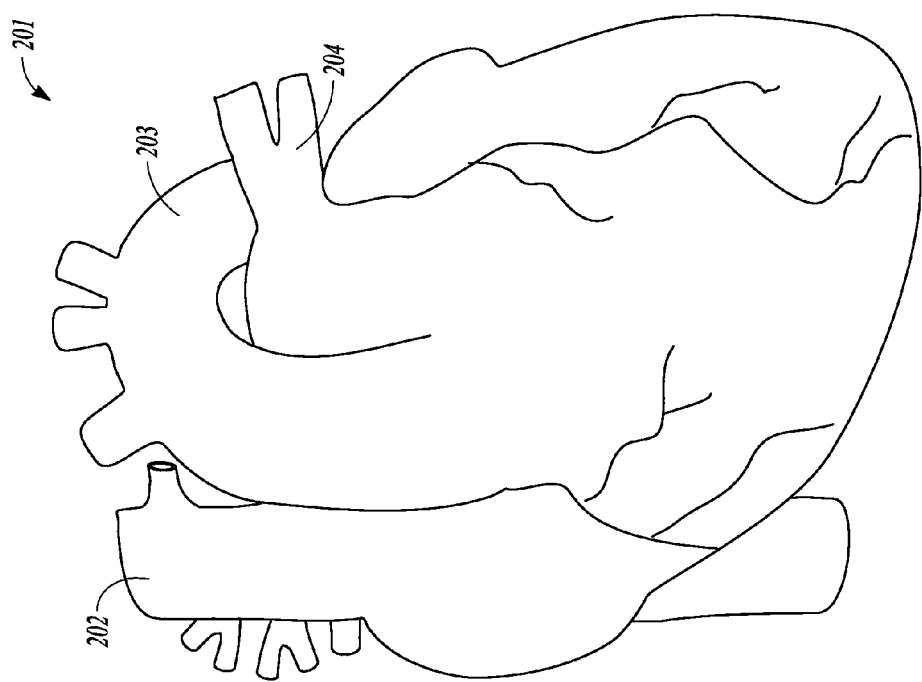
FIG. 2 is an illustration of a heart including the superior vena cava, the aortic arch, and the pulmonary artery.

FIG. 2 illustrates a heart. The heart 201 includes a superior vena cava 202, an aortic arch 203, and a pulmonary artery 204. The pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead described above, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreflex stimulator intravascularly into the pulmonary artery.

Figure 3:
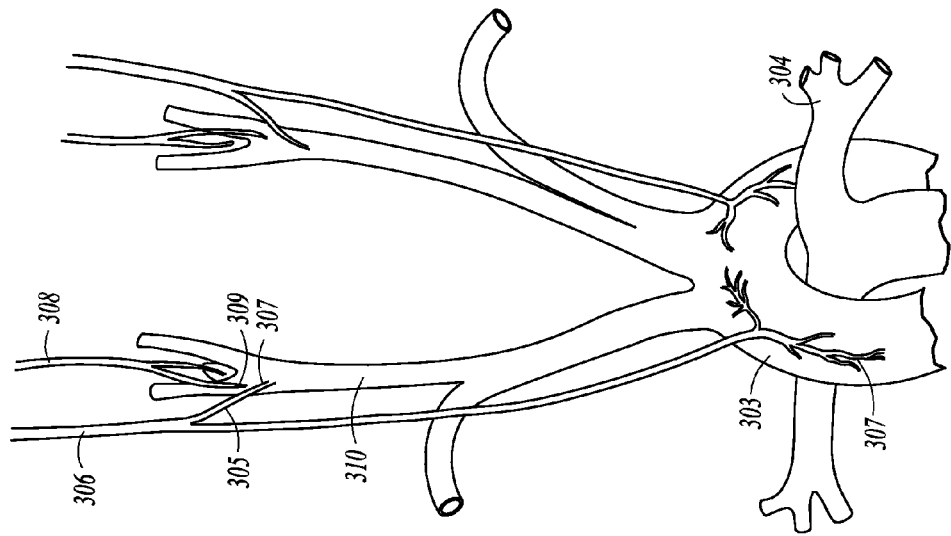
FIG. 3 illustrates baroreceptors in the area of the carotid sinus, aortic arch, and pulmonary artery.

FIG. 3 illustrates baroreceptors in the area of the carotid sinus 305, aortic arch 303, and pulmonary artery 304. The aortic arch 303 and pulmonary artery 304 were previously illustrated with respect to the heart in FIG. 2. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduces pressure. Although not illustrated in the figures, the atrial and ventricular chambers of the heart also include baroreceptors. Cuffs can be placed around afferent nerve trunks, such as the vagal nerve, leading from baroreceptors to vasomotor centers to stimulate the baroreflex. The cuffs can include electrodes for delivering neural stimulation energy. According to various embodiments of the present subject matter, afferent nerve trunks can be stimulated using a cuff or an intravascularly-fed lead positioned in a blood vessel proximate to the afferent nerves.

Pacing therapy includes cardiac contractile electrostimulation. The stimulation is provided as output voltage pulses to cause depolarization of cardiac cells and contraction of the myocardium. Pacing stimulation can be delivered to the heart as pulses of quasi-constant voltage output.

Figure 4:
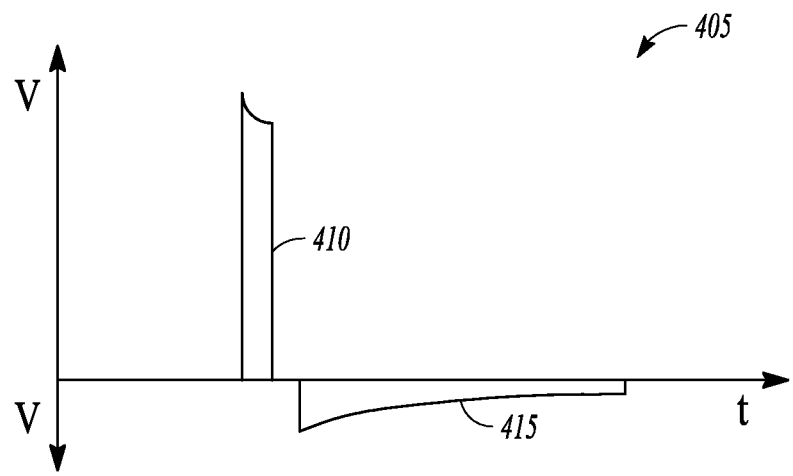
FIG. 4 shows an example of a pacing stimulation pulse.

FIG. 4 shows an example of a pacing stimulation pulse 405. The pacing stimulation pulse 405 can be referred to as a quasi-constant voltage, or a virtually constant voltage, because there can be some droop of the amplitude of the pulse. This droop is the result of the RC time constant of the output circuit.

In some examples, the pacing stimulation pulse can involve two portions. The first portion 410 is to initiate a depolarization of myocardial cells. In some examples, the amplitude of the first portion 410 is programmable. The second portion 415 includes a charge-restoring stimulus to dissipate after-potentials resulting from delivery of the first portion 410 of the pacing stimulation. This can reduce the chance of a DC charge accumulating at the electrode/tissue interface. Without the charge-restoring stimulus, the accumulation of charge can reduce the effectiveness of the first portion of the pacing stimulation.

Figure 5:
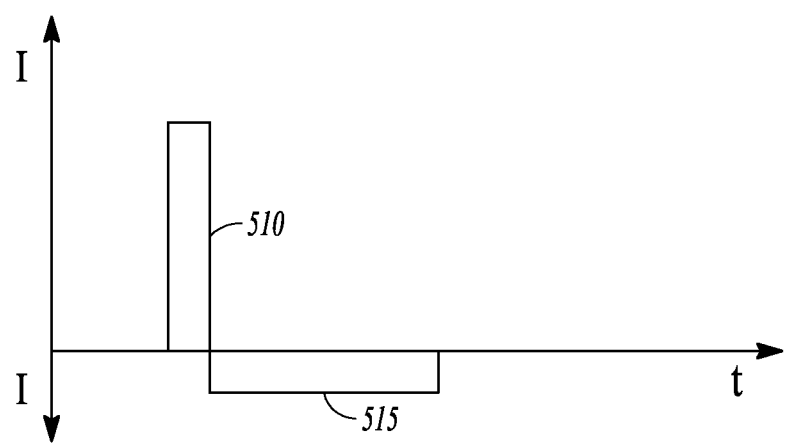
FIG. 5 shows an example of a neural stimulation pulse.

Neural stimulation involves providing energy of constant current to nerves and is not intended to be contractile. FIG. 5 shows an example of a neural stimulation pulse 505. In some examples, the neural stimulation pulse 505 can involve two portions. The first portion 510 and the second portion 515 are current pulses of constant current amplitude. The second portion 515 restores the balance of charge at the electrode/tissue interface. In some examples, the amplitudes of one or both of the first and second portions 510 are programmable. Nerves can adapt to the stimulation, which can result in effectiveness of neural stimulation therapy diminishing over time. The neural stimulation can be modulated to mimic the effects of naturally occurring stimulation and to prevent adaptation of the nerves to the artificial stimulation. For example, the amplitude, frequency, wave morphology, burst frequency and/or duration can be adjusted to abate adaptation.

Figure 6:
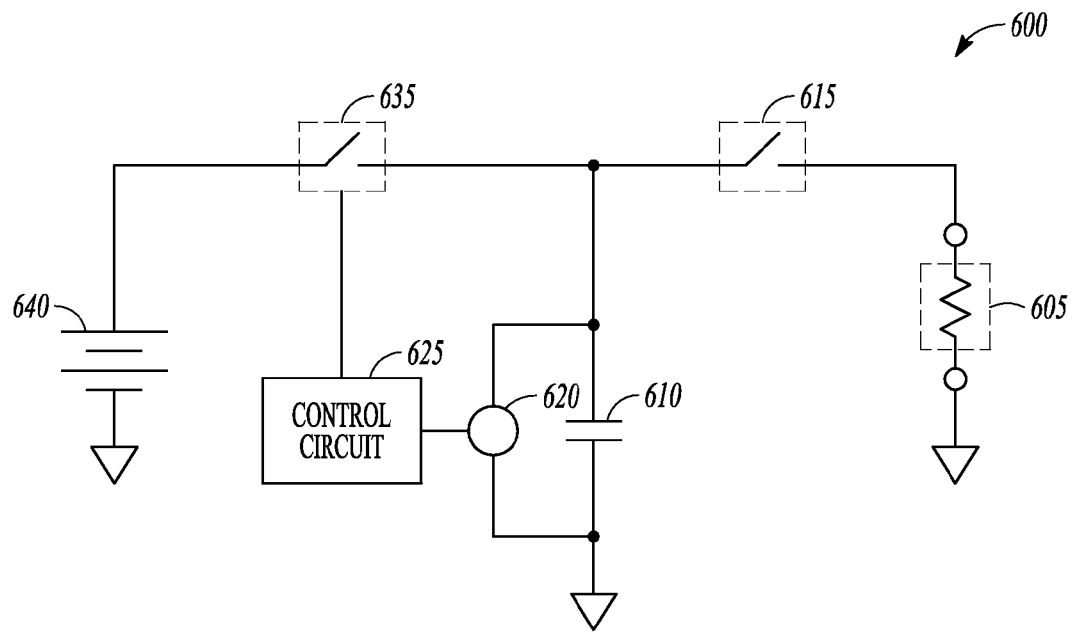
FIG. 6 shows a block diagram of portions of an example of a device therapy circuit that provides quasi-constant current neural stimulation therapy through a load.

FIG. 6 is a block diagram of portions of an example of a device therapy circuit 600 that provides quasi-constant current neural stimulation therapy through a load 605. Examples of the load 605 include, among other things, specific areas of the myocardium and specific areas of the nervous system of a patient or subject. The therapy circuit 600 includes an electrostimulation energy storage capacitor 610 and a circuit path communicatively coupled to the electrostimulation energy storage capacitor 610. To provide energy for the therapy, an energy supply 640 (e.g., a battery) can be used to pre-charge the electrostimulation energy storage capacitor 610.

The therapy circuit 600 includes a current measuring circuit 620 communicatively coupled to the therapy circuit 600 that obtains a measure of quasi-constant current delivered to the load. The therapy circuit 600 also includes a control circuit 625 communicatively coupled to the current measuring circuit 620. The communicative coupling allows the control circuit 625 to communicate signals with the current measuring circuit even though there may be intervening circuitry between the control circuit 625 and the current measuring circuit 620.

The control circuit 625 provides the timing of the therapy. The control circuit 625 may include a processor such as a microprocessor, a digital signal processor, application specific integrated circuit (ASIC), microprocessor, or other type of processor, interpreting or executing instructions in software or firmware. The control circuit 625 can include other circuits or sub-circuits to perform the functions described. These circuits may include software, hardware (e.g., logic circuits), firmware or any combination thereof. Multiple functions can be performed in one or more of the circuits as desired. In some examples, the control circuit 625 can include a state machine implemented in hardware (e.g., logic circuits) to transition the control circuit 625 to different device states that correspond to device functions.

The control circuit 625 initiates the quasi-constant current stimulation by pre-charging the electrostimulation energy storage capacitor 610 using the supply switch 635 and electrically connecting the capacitor 610 to the load 605 via electrodes. Thus, the circuit path provides quasi-constant current neural stimulation through a load from the electrostimulation energy storage capacitor 610. The circuit path begins at the storage capacitor and continues through the load 605. In some examples, the circuit path includes a therapy switch circuit 615. The therapy delivered is quasi-constant current because there can be some droop of the amplitude of the delivered current stimulation pulse.

The control circuit 625 initiates adjustment of the voltage level of the storage capacitor 610 for a subsequent delivery of quasi-constant current according to a comparison of the measured load current to a specified load current value.

The therapy circuit 600 uses a capacitor to store energy for the quasi-constant current neural stimulation therapy. Ideally, inductors would be used to store the energy, but losses associated with inductors make this approach less feasible.

In some examples, the therapy circuit 600 is included in a battery powered device (e.g., an implantable medical device or IMD). Because a capacitor is used for energy storage, there is a need to optimize the amount of energy used to supply the current to the load. To preserve battery energy, the energy stored on the storage capacitor 610 should be reduced to a minimum required to provide the current stimulation to the load and to cover any amount of overhead needed by circuits used to deliver the current stimulation. This required energy varies with the impedance of the load. As the load increases, the voltage of the load increases to maintain the constant current therapy. This increases the required compliance voltage(s). Similarly, as the load decreases, the voltage of the load decreases. The required compliance voltage can be decreased to reduce the energy required to deliver the therapy. It is desired to maintain a compliance voltage that is sufficient for the circuits to work but does not waste current. As an illustrative example, the compliance voltage may be 200 millivolts (mV) above the voltage required for the load.

In some examples, the control circuit 625 recurrently initiates obtaining a measure of the delivered quasi-constant load current and adjusting the voltage level of the storage capacitor to minimize a difference between the measured quasi-constant current and the specified target load current. This allows the control circuit to tune or "dial in" the appropriate voltage level on the storage capacitor to provide the specified load current target as the impedance of the load changes. In some examples, the specified target load current is a programmable therapy parameter. The electrical impedance of the load may vary from patient to patient, may vary from therapy to therapy for the same patient, and may vary during the same delivery of therapy. Thus, it is desirable for the therapy circuit 600 to maintain the target load current over a range of load impedances.

Figure 7:
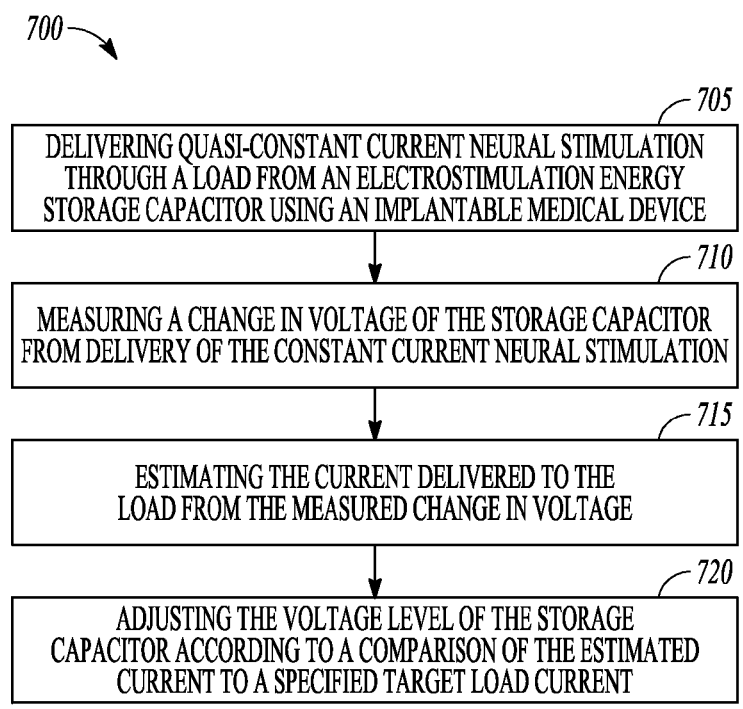
FIG. 7 shows a flow diagram of an example of a method to optimize energy used to deliver quasi-constant current stimulation therapy to a load.

FIG. 7 shows a flow diagram of an example of a method 700 to optimize energy used to deliver quasi-constant current stimulation therapy to a load. At block 705, quasi-constant current neural stimulation is delivered through a load from an electrostimulation energy storage capacitor using an IMD, such as by the therapy circuit 600 in FIG. 6 for example.

Figure 8:
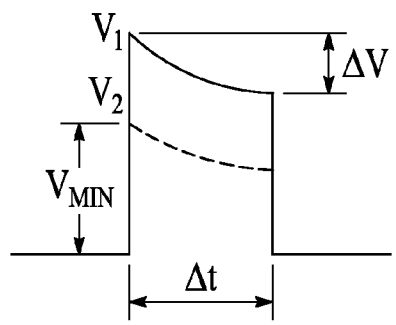
FIG. 8 is an example of a capacitor discharge curve.

At block 710, a change in voltage of the storage capacitor from delivery of the constant current neural stimulation is measured. As current is drawn from the storage capacitor, there is some droop in the voltage on the storage capacitor. This is shown in FIG. 8 where the droop is denoted as $\Delta V$.

At block 715, the current delivered to the load is estimated from the measured change in voltage. In some examples, the current is estimated using the equation for current $I=C \cdot \Delta V/\Delta t$, where I is the current delivered, C is the capacitance of the storage capacitor 610, $\Delta V$ is the measured droop of the voltage of the storage capacitor, and $\Delta t$ is the time over which the voltage droop occurred. In some examples, the $\Delta t$ is the pulse width or pulse duration of the constant current therapy.

At block 720, the voltage level of the storage capacitor is adjusted according to a comparison of the estimated load current to a specified target load current. The voltage on the storage capacitor at the end of the current therapy pulse needs to be at least the minimum voltage Vmin to maintain compliance of the circuitry. An example of this is shown in the capacitor discharge curve of FIG. 8. If the voltage on the storage capacitor starts at voltage V1, the voltage on the storage capacitor will still be greater than the compliance voltage after the voltage droop occurs. If the voltage on the storage capacitor starts at voltage V2, the voltage on the storage capacitor will be less than the compliance voltage after the voltage droop occurs. This may result in the circuitry that delivers the constant current therapy not working properly. In some examples, the voltage level of the storage capacitor is changed to the minimum level required to source the specified current and maintain the compliance voltage (e.g., $\Delta V=I \cdot \Delta t/C$). In some examples, the voltage level of the storage capacitor is incremented or decremented by a specified voltage step. In this way, the optimum voltage for the storage capacitor can be tuned to provide the target load current.

Figure 9:
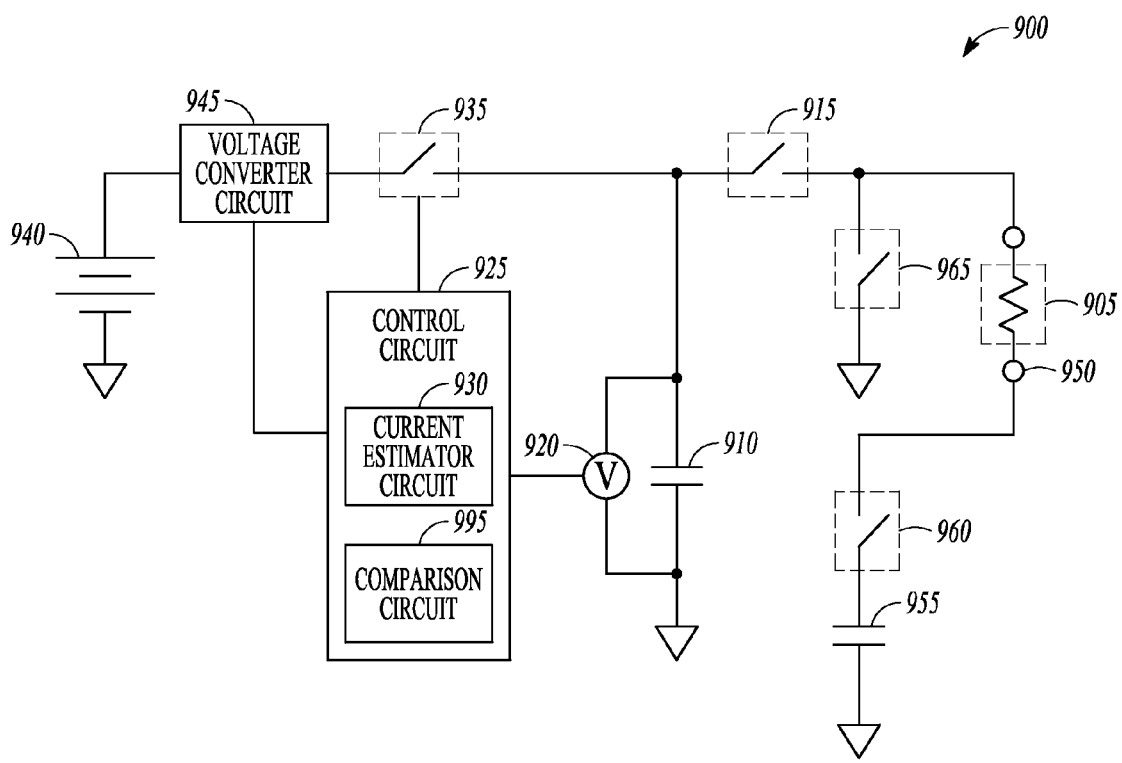
FIG. 9 is a block diagram of portions of another example of a device therapy circuit that provides quasi-constant current neural stimulation therapy through a load.

FIG. 9 is a block diagram of portions of another example of a device therapy circuit 900 that provides quasi-constant current neural stimulation therapy through a load 905. The therapy circuit 900 again includes an electrostimulation energy storage capacitor 910 and a control circuit 925.

The current measurement circuit includes a voltage measurement circuit 920 communicatively coupled to the storage capacitor 910 and a current estimator circuit 930 included in the control circuit 925. The voltage measurement circuit 920 measures a change in voltage of the storage capacitor resulting from delivery of the quasi-constant current neural stimulation. The current estimator circuit 930 estimates the quasi-constant current delivered to the load from the measured change in voltage of the storage capacitor, such as by the method in FIG. 7 for example.

In some examples, the control circuit 925 is configured to initiate an increase in the voltage level of the storage capacitor 910 to a minimum voltage level sufficient to operate the current measurement circuit and to provide the specified load current value. In some examples, the control circuit 925 is configured to initiate a reduction in the voltage level of the storage capacitor to a minimum voltage level sufficient to provide the specified load current value.

According to some examples, the circuit 900 includes a voltage converter circuit 945 (e.g., a DC-DC voltage converter) to change a voltage provided to the storage capacitor 910 via the supply switch 935. The voltage converter circuit 945 may include a programmable voltage reference circuit to provide a changeable reference voltage value. The voltage converter circuit 945 sets the voltage level of the storage capacitor 910 according to the reference voltage value. If the voltage (or a measured fraction of the voltage) of the storage capacitor 910 is less than the programmed voltage reference, the voltage converter circuit 945 increases the voltage on the storage capacitor 910. In some examples, the control circuit 925 initiates a change in the voltage of the storage capacitor 910 by changing the reference voltage value.

In some examples, the control circuit 925 includes a comparison circuit 995 to compare the estimated load current to the specified load current. The control circuit 925 recurrently initiates a comparison of the estimated load current to the specified load current value, recurrently increases the voltage of the storage capacitor by a specified voltage change when the estimated load current is less than the specified load current value, and recurrently decreases the voltage of the storage capacitor 910 by the specified voltage change when the estimated load current is greater than the specified load current value.

According to some examples, the therapy circuit 900 includes a recharge circuit communicatively coupled to a port 950 configured for electrical connection to the load 905. The recharge circuit may include a recharge capacitor 955. In some examples, the recharge circuit includes a recharge switch 960 and a return switch 965. The control circuit 925 can initiate a delivery of biphasic electrical neural therapy to the load 905. The biphasic therapy includes quasi-constant current neural stimulation during a first phase of the biphasic electrical neural therapy and includes delivery of a charge-restoring pulse in a second phase of energy delivery.

Figure 10:
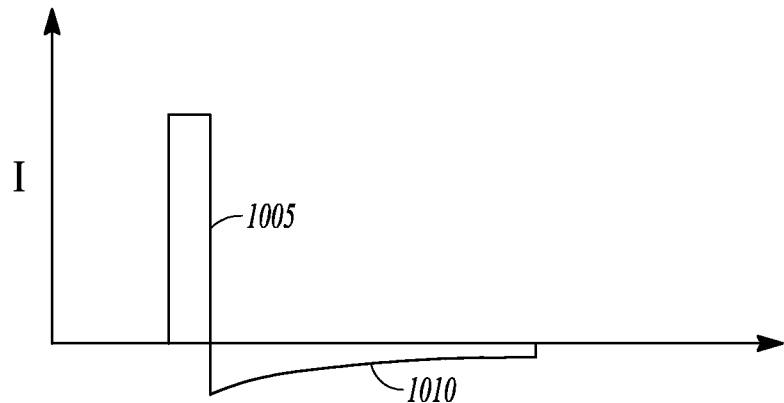
FIG. 10 shows an example of a hybrid current/charge-restoring therapy pulse.

FIG. 10 shows an example of such a hybrid current/charge-restoring therapy biphasic pulse. Quasi-constant current is delivered during the first phase 1005 of the biphasic electrical neural therapy. The quasi-constant current neural stimulation is delivered through the load 905 using energy stored on the storage capacitor 910. The recharge capacitor 955 stores the electrical energy from the quasi-constant current neural stimulation during the first phase. A charge-restoring pulse is delivered during the second phase 1010 of the biphasic electrical neural therapy. To generate the charge-restoring pulse, the recharge capacitor 955 discharges its stored electrical energy to the load 905. In some examples, the return switch 965 is open during the first phase and is closed during the second phase. In some examples, the control circuit 925 measures the change in voltage of the storage capacitor 910 during the first phase of the biphasic electrical neural therapy.

Note that, in comparison to the all current waveform of FIG. 5, energy for the delivery of the biphasic neural therapy is reduced by using a recharge capacitor in place of the current source during the second phase of the pulse. Thus, charge balance is maintained at the lead-tissue interface for reduced energy cost of an all-current waveform. In the example shown, closing or otherwise activating switches 960 and 965 causes the recharge circuit to deliver a recharge-phase of the pulse having a polarity opposite to the polarity of the quasi-constant current neural stimulation. The second recharge-phase pulse restores charge balance at the electrode-tissue interface.

Figure 11:
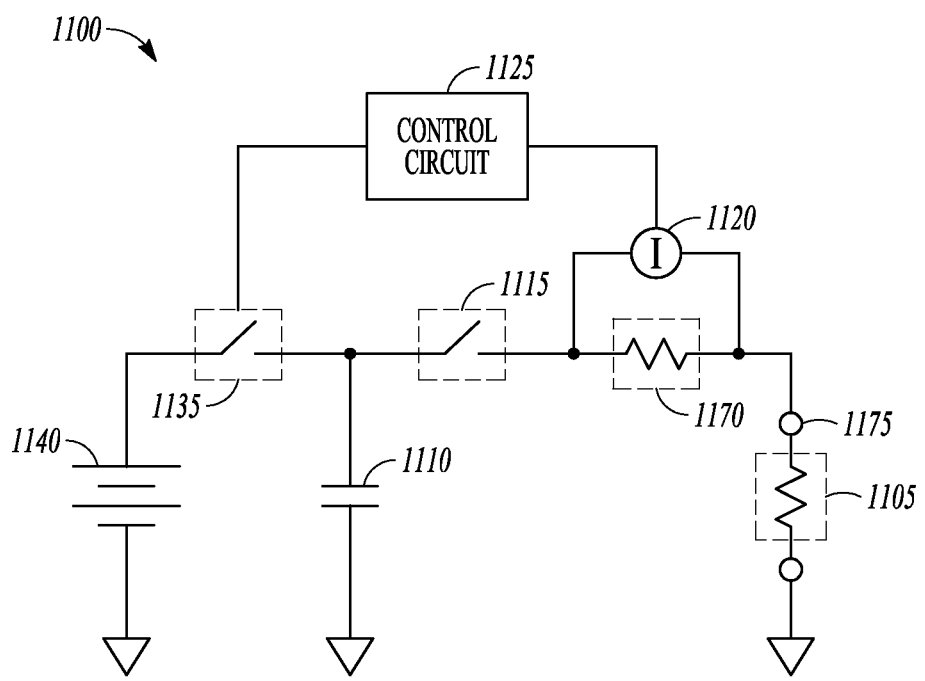
FIG. 11 is a block diagram of portions of another example of a device therapy circuit that provides quasi-constant current neural stimulation therapy through a load.

FIG. 11 is a block diagram of portions of another example of a device therapy circuit 1100 that provides quasi-constant current neural stimulation therapy through a load 1105. The therapy circuit 1100 again includes an electrostimulation energy storage capacitor 1110 and a control circuit 1125. The control circuit 1125 initiates the quasi-constant current stimulation by pre-charging the electrostimulation energy storage capacitor 1110 using the supply switch 1135 and electrically connecting the capacitor 1110 to the load 1105 via electrodes.

The circuit path includes a sense resistor 1170 arranged in series with a port 1175 configured for electrical connection to the load 1105. The current monitoring circuit 1120 is communicatively coupled to the sense resistor 1170. The current monitoring circuit 1120 measures a voltage across the sense resistor 1170 and obtains the measure of quasi-constant current delivered to the load using the measured voltage. The control circuit 1125 initiates adjustment of the voltage level of the storage capacitor 1110 for a subsequent delivery of quasi-constant current according to a comparison of the measured load current to a specified target load current value. In some examples, the control circuit 1125 initiates a reduction in the voltage level of the storage capacitor to a minimum voltage level sufficient to operate the current monitoring circuit 1120 and sense resistor 1170, and to provide the specified load current value.

Figure 12:
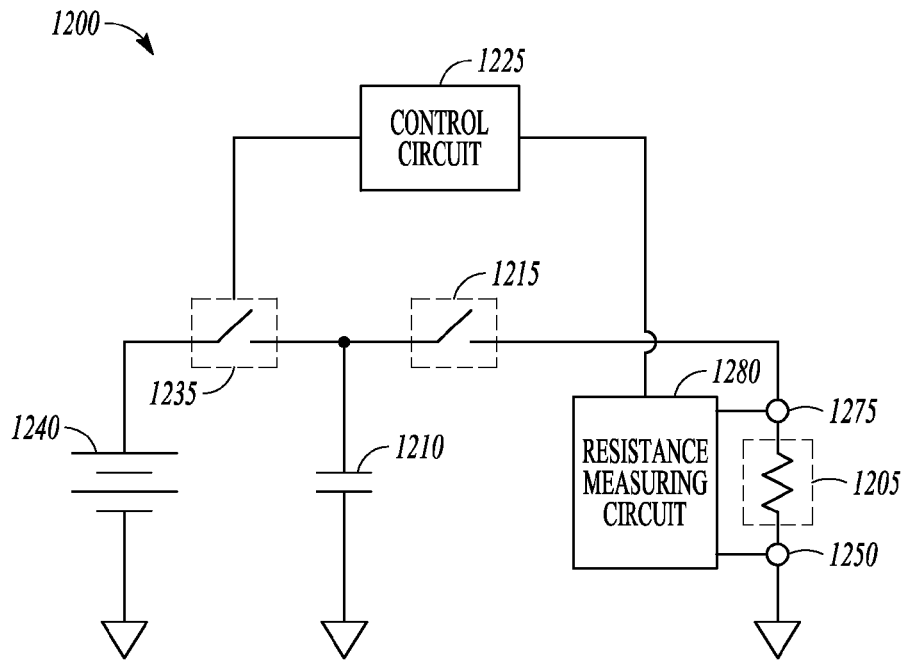
FIG. 12 is a block diagram of portions of another example of a device therapy circuit that provides quasi-constant current neural stimulation therapy through a load.

FIG. 12 is a block diagram of portions of another example of a device therapy circuit 1200 that provides quasi-constant current neural stimulation therapy through a load 1205. The therapy circuit 1200 again includes an electrostimulation energy storage capacitor 1210 and a control circuit 1225. The control circuit 1225 initiates the quasi-constant current stimulation from energy stored on the electrostimulation energy storage capacitor 1210.

The therapy circuit 1200 includes a resistance measuring circuit 1280 communicatively coupled to the circuit path to obtain a measure of resistance of the load 1205. The control circuit 1225 is configured to initiate adjustment of the voltage level of the storage capacitor 1210 for a delivery of quasi-constant current according to the measure of resistance and the target load current. In some examples, the resistance can be measured by applying a specified non-stimulating excitation current pulse across the load, such as between ports 1275 and 1250. The excitation current is non-stimulating because it has an amplitude lower than the minimum amplitude for pacing stimulation, i.e., it has low enough amplitude that it does not trigger a heart depolarization or stimulate a nerve. The resulting voltage between the ports is then measured. The measured voltage is divided by the excitation current to obtain the resistance. The control circuit 1225 sets the voltage of the storage capacitor 1210 to the voltage necessary to provide the target load current. In some examples, the voltage includes sufficient voltage to provide compliance for any circuits in the circuit path.

Examples of systems and methods of painless measurement of defibrillation lead impedance are found in Linder et al., U.S. Pat. No. 6,317,628, "Cardiac Rhythm Management System with Painless Defibrillation Lead Impedance Measurement," filed Jan. 25, 1999, which is incorporated herein in its entirety.

Figure 13:
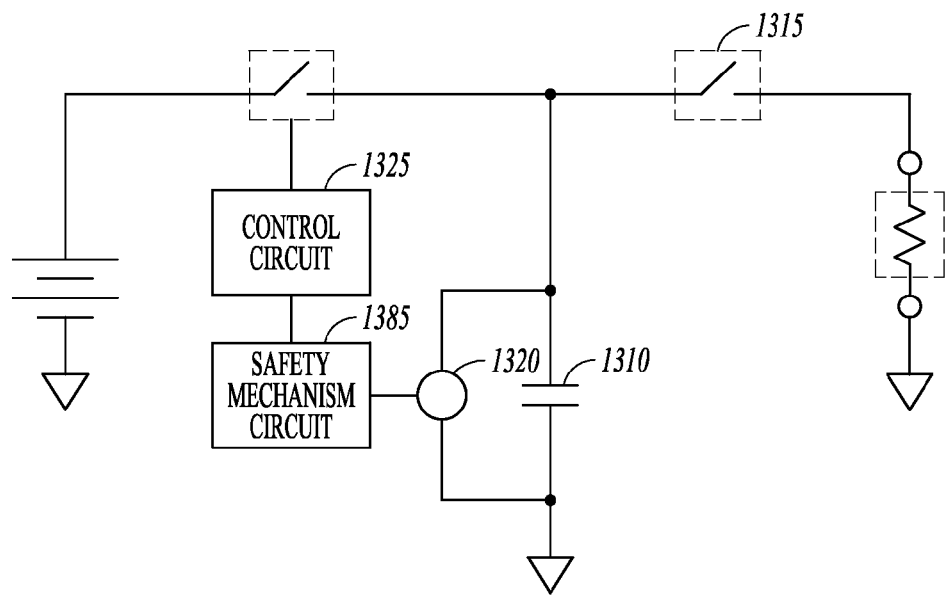
FIG. 13 is a block diagram of portions of the example device therapy circuit of FIG. 6 and including a safety mechanism circuit.

In some examples, a safety mechanism circuit is used to guard against excessive energy (e.g., runaway current) being delivered to the patient or subject. FIG. 13 is a block diagram of portions of the example therapy circuit of FIG. 6 with a safety mechanism circuit 1385. The safety mechanism circuit 1385 is communicatively coupled to the current measuring circuit 1320 and the control circuit 1325. The safety mechanism circuit 1385 monitors delivery of electrical energy during the quasi-constant current stimulation. The control circuit 1325 ends the constant current stimulation when the safety mechanism circuit 1385 indicates that the electrical energy exceeds a specified energy level threshold.

In some examples, the safety mechanism circuit 1385 is communicatively coupled to the voltage measuring circuit 920 of FIG. 9. The safety mechanism circuit 1385 may determine that the electrical energy exceeds a specified energy level threshold if the change in voltage of the storage capacitor 1310 exceeds a threshold voltage change value. In certain examples, the safety mechanism circuit 1385 includes a comparator circuit to detect a change in voltage that exceeds the threshold value. In some examples, the safety mechanism circuit 1385 detects a rate of discharge of the electrical energy that exceeds a specified threshold discharge rate.

In some examples, the safety mechanism circuit 1385 is communicatively coupled to the sense resistor 1170 in FIG. 11 and monitors current through the sense resistor 1170. In certain examples, the safety mechanism circuit 1385 includes an amplifier coupled to the sense resistor 1170. The output of the sense amplifier is coupled to a first input of a comparator circuit. The second input of the comparator is coupled to a voltage reference circuit. An over-current condition is detected when the voltage drop across the sense resistor exceeds the voltage value of the voltage reference. In some examples, the voltage reference is programmable.

When the safety mechanism circuit indicates that the electrical energy delivered exceeds a specified energy level threshold (e.g., an excessive voltage change at the capacitor or an over-current condition at the sense resistor or the load), the control circuit 1325 ends the quasi-constant current stimulation. In certain examples, the control circuit 1325 opens therapy switch 1315 to end the quasi-constant current stimulation by immediately truncating the current therapy pulse. In certain examples, the control circuit 1325 terminates charging of the storage capacitor 1310 (such as by deactivating a voltage converter circuit 945 of FIG. 9) to end the therapy.

Devices and methods are described herein to efficiently operate a quasi-constant current therapy delivery system. This improvement automatically finds the minimum overhead operating voltage required for the circuitry used to deliver the quasi-constant current stimulation. The use of a hybrid therapy pulse also reduces the energy used to maintain charge balance at the lead-tissue interface.

Power Supply Management

As explained previously herein, an ambulatory neural stimulation device can be battery powered. If the ambulatory medical device is an IMD, the device may need to be explanted after the battery energy is depleted. For this reason it is desirable to manage the energy of the battery to extend the active life of the IMD. Longevity of the battery energy can depend on many factors. One of the most prevalent factors is the setting of the voltage level or voltage value of the supply to the therapy circuit that provides the current stimulation pulses. Setting the supply voltage to a low value can help increase battery longevity.

As described previously herein, the neural stimulation pulses are provided to a "load" that can include, among other things, specific areas of the myocardium and specific areas of the nervous system. When setting the voltage value for the supply voltage, the output current amplitude, the output load impedance, and the voltage margin or overhead needed for the therapy circuit to function should be taken into account.

Figure 14:
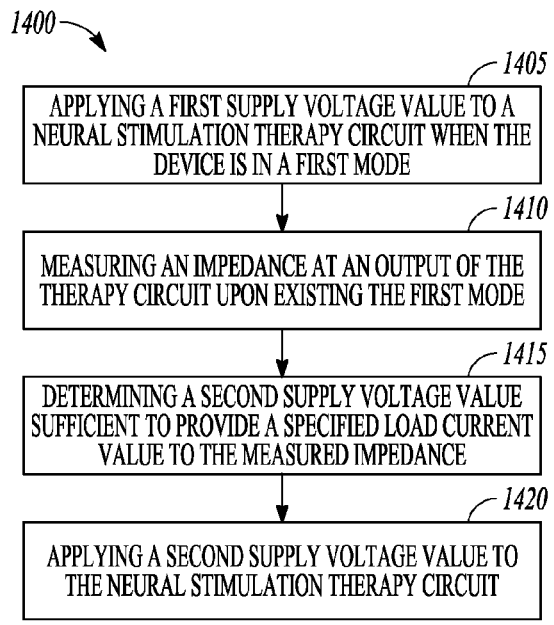
FIG. 14 shows an example of a flow diagram of a method for controlling the operation of an ambulatory medical device.

FIG. 14 shows an example of a flow diagram of a method 1400 for controlling the operation of an ambulatory medical device. At block 1405, a first supply voltage value is applied to a neural stimulation therapy circuit of an ambulatory medical device when the ambulatory medical device is in a first mode. The first mode can be a storage mode. The device may be placed (e.g., programmed) in storage mode prior to activation for use by a patient. For instance, an IMD may be placed in storage mode after final testing as part of manufacturing. Storage mode is a low energy mode that minimizes the drain on the battery. Many functions such as therapy output are disabled when the device is placed in storage mode. The first mode can also be any mode where the therapy output is disabled. A supply voltage of zero volts can be applied to the neural stimulation therapy circuit when the therapy output is disabled.

At block 1410, the impedance at the output of the neural stimulation therapy circuit is measured by the device upon exiting the first mode. An IMD may exit the first mode when a command to exit storage mode is received by the IMD such as through wireless telemetry. A wearable medical device may exit storage mode when a command to do so is received by the device through either wireless telemetry or a user interface. If the first mode is another mode where therapy is disabled, the device may exit the first mode when the therapy is subsequently enabled. The impedance may be measured by applying a current to a load and measuring the resulting voltage. Such an approach is described in the previously mentioned U.S. Pat. No. 6,317,628.

At block 1415, a second supply voltage value is determined. The second supply voltage value is determined using the measured impedance, and is sufficient for the therapy circuit to provide a specified load current to the measured impedance. An integrated circuit that provides a current to a load (e.g., a current source) has an associated compliance voltage or voltages. This compliance voltage can be viewed as a range over which the circuit can provide the intended current to the load. The compliance voltage includes the voltage resulting from providing the current to the load plus overhead voltage ($V_{OH}$) needed for operation of the circuit. If the load impedance is considered a resistance, the second supply voltage value can be determined as $V_{SUPPLY} = (R_{LOAD} * I_{LOAD}) + V_{OH}$.

Figure 15:
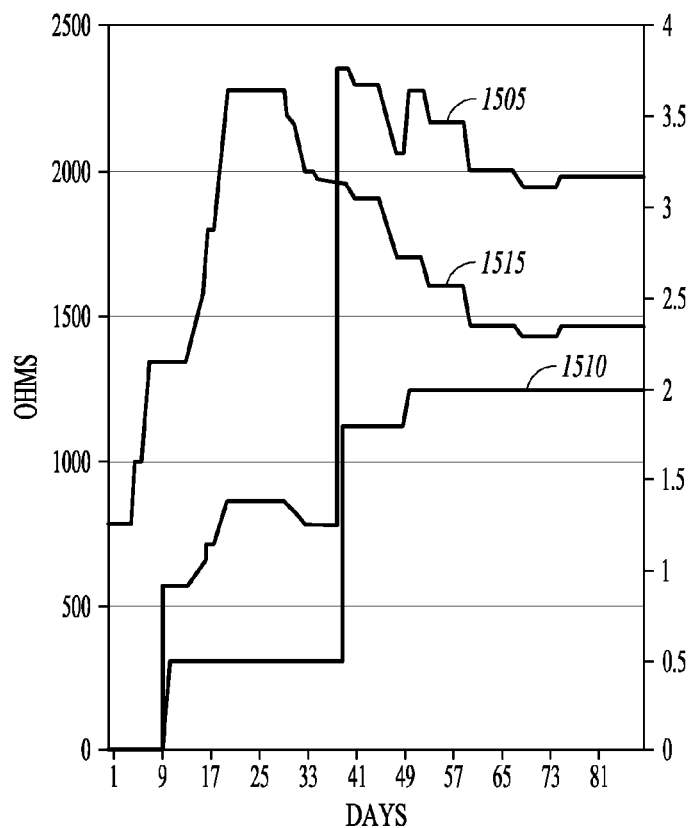
FIG. 15 illustrates an example of impedance changing with time.

In practice, it may be desirable to include additional margin to $V_{OH}$ when determining the supply voltage value. This can allow for any variance in processes used to manufacture the integrated circuits and for variations in integrated circuit variations due to temperature changes. Additional voltage margin is also useful to accommodate variation in load impedance due to a healing process that encapsulates implanted electrodes. This encapsulation tends to increase the load impedance over a relatively long period of time. An illustration of changing load impedance is shown in FIG. 15. The Figure shows a graph of load impedance 1515 versus time. Also shown are a graph of load current 1510 and a graph of supply voltage 1505. The graphs show that the load impedance 1515 increases after the device is implanted and later decreases to an impedance that is still higher than the impedance seen at time of implant. The graphs also show that the healing process results in a load impedance that can change over many days. Consequently, it may be useful to perform daily measurements with the ambulatory medical device and make daily adjustments to the supply voltage.

Additional impedance changes occur in the short term due to changes in body position or changes in body motion. For instance, load impedance can change when a patient moves from to an upright position due to shifting position of internal organs. The shifting may result in electrodes having more or less contact with the tissue target. Heart beats or pulse pressure waves through the carotid artery can cause a slight movement in the lead causing a brief change in impedance. Use of a voltage margin when setting the supply voltage can account for these changes in the load impedance. It may also be useful to perform impedance measurements and supply voltage adjustments continuously or nearly continuously in order to best tune the balance between power consumption and avoiding the voltage compliance limit.

Returning to FIG. 14, at block 1420, the determined supply voltage value is applied to the therapy circuit. The therapy circuit may be enabled by the application of the second voltage value, or a separate signal may be used to enable the therapy circuit.

Figure 16:
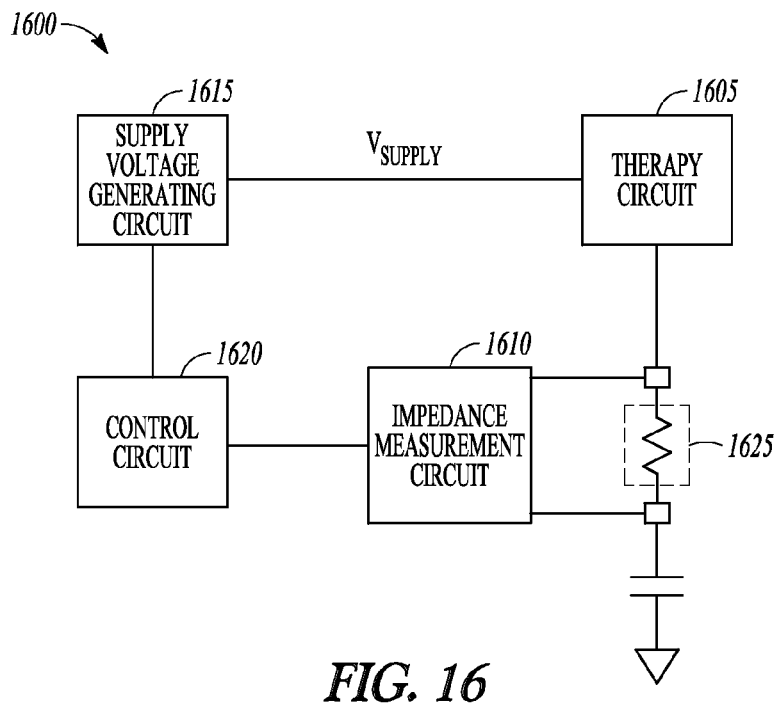
FIG. 16 is a block diagram of portions of an example of an ambulatory medical device.

FIG. 16 is a block diagram of portions of an example of an ambulatory medical device that manages the power supply for neural stimulation. The device 1600 includes a therapy circuit 1605, an impedance measurement circuit 1610, a supply voltage generating circuit 1615 and a control circuit 1620. The therapy circuit 1605 provides a neural stimulation current at an output of the therapy circuit 1605. In some examples, the therapy circuit 1605 includes a current source circuit to provide a specified (e.g., programmed) neural stimulation current to the load 1625. In some examples, the therapy circuit 1605 and the load 1625 are arranged differently and the therapy circuit 1605 includes a current sink circuit.

The impedance measurement circuit 1610 measures a value of impedance at the output of the therapy circuit 1605. In some examples, the impedance measurement circuit 1610 includes the resistance measuring circuit 1280 previously described previously herein regarding FIG. 12 and determines a resistance seen at the load 1625. The supply voltage generating circuit 1615 provides an adjustable supply voltage value to the therapy circuit 1605.

The control circuit 1620 can control the functional mode of the device. When an indication (e.g., a signal or a decoded command) is received to exit the first mode and enter a second mode where therapy is enabled, the control circuit 1620 initiates an impedance measurement by the impedance measurement circuit 1610. The control circuit 1620 determines the second supply voltage value using the measured impedance. The second supply voltage value is sufficient to operate the therapy circuit and to provide a specified load current value to the measured impedance. In some examples, the second supply voltage is calculated using a specified load current, the measured impedance and a value for voltage overhead of the therapy circuit.

The control circuit 1620 then initiates a change from the first supply voltage value to the second supply voltage value. The control circuit 1620 may initiate the change immediately or may wait until delivery of load current is enabled. In some examples, the therapy circuit 1605 may be used to provide current for the impedance measurement. In this case, the control circuit 1620 may first initiate a change in the supply voltage to a third intermediate supply voltage value to accomplish the impedance measurement and then initiate the change to the second supply voltage value when the impedance has been measured. In some examples, the control circuit 1620 waits to initiate an impedance measurement when delivery of the load current is enabled.

The therapy circuit 1605 can include a programmable current circuit that provides a programmable load current value to the output of the therapy circuit 1605. For instance, the therapy circuit 1605 can include a current mirror circuit (not shown). In a current mirror, a number of transistors are used to mirror the current of a bias transistor. Changing the number of transistors used to mirror the current can change the load current value. In some examples, the control circuit 1620 re-determines the second supply voltage value when the programmable load current is changed.

Figure 17:
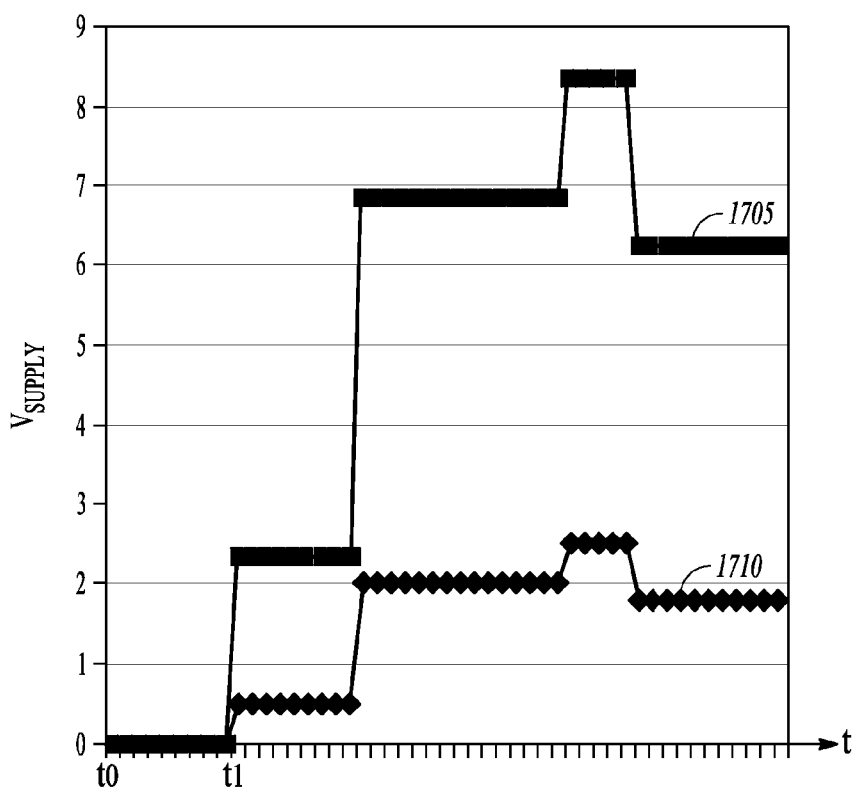
FIG. 17 shows an example of changing the supply voltage value.

FIG. 17 shows an example of changing the supply voltage value when the specified load current is changed. At time $t_0$, the device exits the first mode. As shown in the Figure, the supply voltage 1705 and the load current 1710 remain at zero until therapy is enabled at time $t_1$. Based on the specified value of load current, $V_{SUPPLY}$ is set to about 2.5 Volts. At subsequent reprogramming of the load current 1710, the control circuit 1620 initiates a change in the supply voltage 1705.

Returning to FIG. 16, the supply voltage generating circuit 1615 can include a voltage converter circuit to generate the supply voltage. As explained previously herein, the control circuit 1620 can initiate a change in the supply voltage value by changing a reference voltage value.

Figure 18:
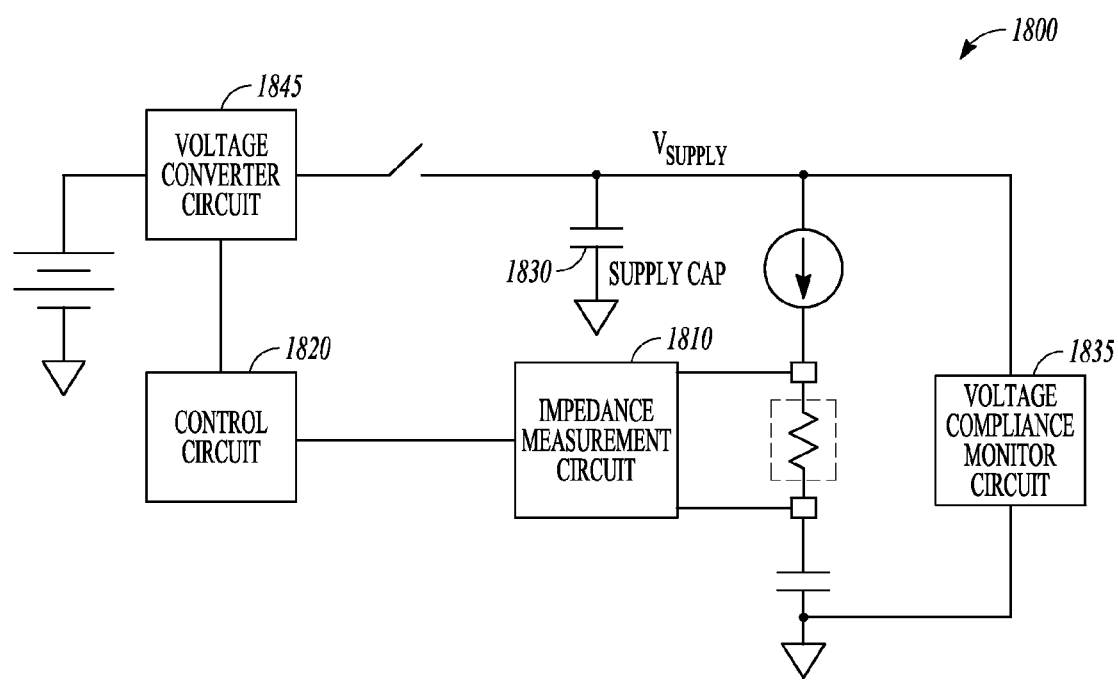
FIG. 18 shows a block diagram of portions of another example of an ambulatory medical device.

FIG. 18 shows a block diagram of portions of another example of an ambulatory medical device 1800 that manages the power supply for neural stimulation. The supply voltage generating circuit includes a voltage converter circuit 1845 that generates the supply voltage on a supply capacitor 1830. The voltage converter circuit 1845 may set the supply voltage according a changeable voltage reference value. The control circuit 1820 can initiate adjustment of the supply voltage of the supply capacitor 1830 from the first supply voltage value to the second supply voltage value by changing the reference voltage value.

FIG. 18 also shows a voltage compliance monitor circuit 1835 that detects when the supply voltage is less than the minimum voltage necessary to operate the therapy circuit and provide the specified load current value to the measured impedance (e.g., $V_{SUPPLY} \leq (R_{LOAD} * I_{LOAD}) + V_{OH}$). The control circuit 1820 initiates an increase in the second supply voltage value when the second supply voltage value is less than the minimum voltage.

Figure 19:
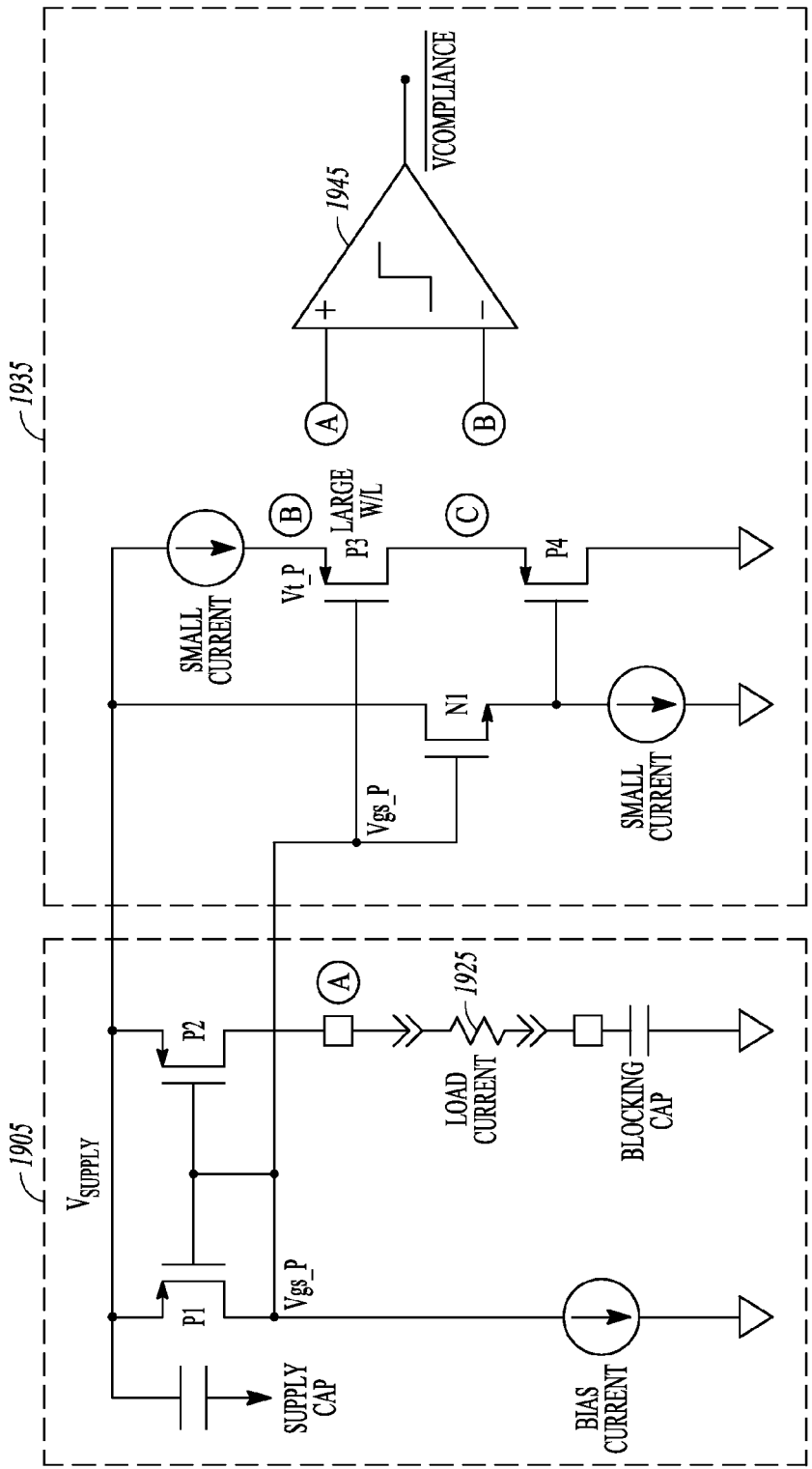
FIG. 19 shows an example of a voltage compliance monitor circuit.

FIG. 19 shows an example of a voltage compliance monitor circuit 1935. The Figure also shows portions of a therapy circuit 1905 that includes a current source to provide a specified neural stimulation therapy current to the load. The current source includes a current mirror topology. For a metal-oxide semiconductor field effect transistor (MOSFET) current mirror as in the example, compliance is achieved when the drain-to-source voltage Vds exceeds the gate-to-source voltage Vg minus the MOSFET threshold voltage Vt (e.g., Vds>Vgs−Vt). Because Vgs and Vt vary with process, temperature and supply voltage, it is desirable to have a circuit that constantly tracks these characteristics to determine whether the current source is being operated within its compliance.

In the example shown, the voltage compliance monitor circuit 1935 indicates when the compliance limit is reached. The circuit creates a reference voltage that tracks Vgs and Vt. This reference voltage, shown as node "B" in the Figure, can be compared with the current source output voltage, node "A" in the Figure, to indicate when the circuit is not capable of delivering the intended current output. When the voltage at node "A" is greater than the voltage at node "B" the current source is not operating within its voltage compliance range. A comparison circuit (e.g., a comparator 1945) can indicate when A>B and the current source is not in compliance.

P-type transistors P1 and P2 form the current mirror circuit. The current labeled BIAS CURRENT will be mirrored from P1 to P2, if P1 and P2 are matched (e.g., have identical layouts and are located in close proximity). One or both of P1 and P2 can also have multiple transistor instances in order to scale the load current. For example, if there is one P1 and two P2's connected in parallel then the current in P2 will be twice the current in P1, and twice the current of P1 will be delivered to the load 1925. Likewise if there are two P1's connected in parallel and one P1 then the current in P2 will be half the current in the two P1 transistors. Due to the negative voltages for a P-channel MOSFET, this mirroring will be accurate if Vds2<Vgs2−Vtp, where Vtp is the threshold voltage of transistor P2. Substituting the circuit node names of the Figure, this relationship becomes A−VSUPPLY<Vgs_P−VSUPPLY−Vtp, which reduces to A<Vgs_P−Vtp.

The purpose of node "B" is to track Vgs_P with a Vtp offset, in order to produce the Vgs_P−Vtp reference level that node "A" can be compared against. The circuit stage with P3 is a P-channel source follower. P4 is used to hold the drain of P3, indicated in the Figure as node "C", at a voltage approximately equal to Vgs_P, which helps keep the Vds of P3 similar to P1. (N1 and P4 are not strictly necessary for the circuit to function, but including them can improve accuracy.) The voltage at node C can be expressed as C=Vgs_P−Vtn−Vtp, which is approximately equal to Vgs_P (if Vtn≈Vtp). This relation is enforced by the N1 N-channel source follower, which creates a Vtn offset to drive the gate of P4. The bias current in the N1 and P3 stages is small in order to minimize the excess Vgs voltages and achieve the Vtp/Vtn offsets.

The current in a saturated MOSFET, Ids, is Ids=k'*W/L* $(V_{gs}-V_t)^2$, where k' is a process dependent parameter, W is the gate width and L is the gate length of the MOSFET. By setting Ids small and a large W/L ratio then $(V_{gs}-V_t)^2$ must be small, and hence $V_{gs} \approx V_t$. The voltage at node "B" is B=Vgs_P−Vgs3≈Vgs_P−Vtp. The voltage at node "B" represents the maximum voltage that node "A" can reach before the current source compliance limit is reached. As explained previously herein, non-compliance is indicated in this example when node "A" is more positive than node "B."

When the voltage compliance monitor circuit 1935 detects that the second supply voltage value is less than the minimum voltage necessary to operate the therapy circuit and provide the specified load current value to the measured impedance (non-compliant), the control circuit may incrementally increase the second supply voltage value in steps (e.g., a programmable step size) until the circuit becomes compliant (e.g., the comparator output indicates that the voltage at node A is less than the voltage at node B).

In some examples, the control circuit may adjust the $V_{SUPPLY}$ voltage to an optimum to preserve battery life. For instance, if the voltage compliance monitor circuit 1935 detects that the second supply voltage value is greater than the minimum voltage necessary to operate the therapy circuit and provide the specified load current value to the measured impedance (is compliant), the control circuit may incrementally decrease the second supply voltage value in steps. If the voltage compliance monitor circuit 1935 indicated that the decreasing has made the circuit non-compliant, the control circuit may increase $V_{SUPPLY}$ by a specified margin. Other methods can be used to monitor compliance.

Figure 20:
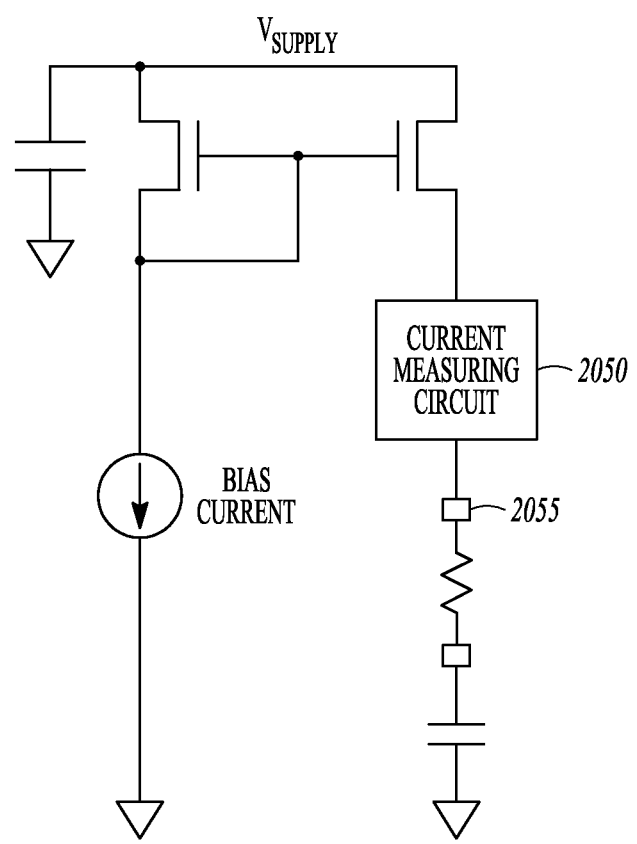
FIG. 20 shows portions of another example of a compliance monitoring circuit.

FIG. 20 shows portions of another example of a compliance monitoring circuit. The example includes a current measuring circuit 2050 communicatively coupled to the output of the current source of the therapy circuit. The current measuring circuit 2050 detects whether a delivered load current is less than the specified load current. In some examples, the current measuring circuit includes a sense resistor in series with a port 2055 configured for electrical connection to the load. The sense resistor can be arranged between the current source and the load or between the load and circuit ground. To determine the load current, the current measuring circuit 2050 measures the voltage at the load having the measured impedance and can use Ohm's Law to determine the current. To measure the voltage of the sense resistor, the current measuring circuit 2050 may include a digital to analog circuit (DAC). A comparison circuit (e.g., a comparator) can be used to compare the output of the DAC to the voltage of the sense resistor. The control circuit changes the DAC until there is a match between the DAC output and the sense resistor voltage.

Using the measured current, the current measuring circuit 2050 can detect whether the delivered load current value is less than the specified load current value. The control circuit may increase the supply voltage when it is determined that the delivered load current value is less than the specified load current value. The control circuit may incrementally increase the supply voltage value in steps to move the measured load current toward the target specified load current, and recheck the current until the current matches the load current. In some examples, the control circuit generates an alert when the supply voltage generating circuit is unable to generate a supply voltage to cause the measured load current to match the specified load current. The alert is provided to a user or process. In certain examples, the alert includes an audible or visible alarm. In certain examples, the alert is communicated to a second separate device.

The control circuit may recurrently initiate an impedance measurement. The impedance measurements may be initiated periodically (e.g., hourly, daily, etc.), or may be initiated when therapy is enabled. In some examples, the impedance is not measured until after a post-implantation healing period has elapsed. In some examples, the control circuit recurrently initiates a series of impedance measurements during a specified time duration. The time duration can be specified by elapsed time (e.g., measurements over an hour) or as a certain number of measurements (e.g., ten measurements). In this way, a range of impedance measurements can be obtained. The impedance measurement used to determine the supply voltage value can be the maximum impedance value of the measured range. This may reduce the chance that the compliance limit will be reached during delivery of the neural stimulation therapy. The compliance of the therapy circuit can also be recurrently monitored, such as when a current pulse is delivered or monitored periodically.

The method and devices described allow for managing the supply voltage level for current stimulation. This can lead to increased battery longevity of an ambulatory medical.

ADDITIONAL NOTES AND EXAMPLES

Example 1 can include subject matter (such as an ambulatory medical device) comprising a therapy circuit configured to provide a neural stimulation current at an output of the therapy circuit, an impedance measurement circuit configured to measure a value of impedance at the output of the therapy circuit, a supply voltage generating circuit configured to provide an adjustable supply voltage value to the therapy circuit including a first supply voltage value when in a first mode, a control circuit communicatively coupled to the therapy circuit, the impedance measuring circuit, and the supply voltage generating circuit. The control circuit, upon receiving an indication to exit the first mode, is configured to: initiate an impedance measurement by the impedance measurement circuit, determine a second supply voltage value using the impedance measurement (wherein the second supply voltage value is sufficient to operate the therapy circuit and to provide a specified load current value to the measured impedance), and initiate a change from the first supply voltage value to the second supply voltage value.

In Example 2, the subject matter of Example 1 optionally includes a therapy circuit having a programmable current circuit configured to provide a programmable load current value to the output of the therapy circuit, and the control circuit is optionally configured to re-determine the second supply voltage value when the programmable load current value is changed.

In Example 3, the subject matter of one or any combination of Examples 1 and 2 optionally includes a voltage compliance monitor circuit configured to detect when the second supply voltage value is less than the minimum voltage necessary to operate the therapy circuit and provide the specified load current value to the measured impedance, and the control circuit is optionally configured to incrementally increase the second supply voltage value when the second supply voltage value is less than the minimum voltage.

In Example 4, the subject matter of Example 3 optionally includes a voltage compliance monitor circuit configured to detect when the second supply voltage value is greater than the minimum voltage necessary to operate the therapy circuit and provide the specified load current value to the measured impedance; and the control circuit is optionally configured to incrementally decrease the second supply voltage value when the second supply voltage value is greater than the minimum voltage.

In Example 5, the subject matter of one or any combination of Examples 1-4 optionally includes a control circuit configured to recurrently initiate an impedance measurement, recurrently calculate the minimum voltage necessary to operate the therapy circuit and provide the specified load current value to the measured impedance, and adjust the second supply voltage to be at least equal to the calculated minimum voltage.

In Example 6, the subject matter of one or any combination of Examples 1-5 optionally includes a current measuring circuit communicatively coupled to the output of the therapy circuit and configured to detect whether a delivered load current value is less than the specified load current value, and the control circuit is optionally configured to incrementally increase the second supply voltage when determining that the delivered load current value is less than the specified load current value.

In Example 7, the subject matter of Example 6 optionally includes a current measuring circuit having a sense resistor in series with a port configured for electrical connection to the load, and the current measuring circuit is optionally configured to measure a voltage across the sense resistor to detect whether the delivered load current value is less than the specified load current value.

In Example 8, the subject matter of one or any combination of Examples 1-7 optionally includes a control circuit configured to recurrently initiate an impedance measurement during a specified time duration to obtain a range of impedance values, and calculate the minimum voltage using the maximum impedance value of the obtained range of impedance values.

In Example 9, the subject matter of one or any combination of Examples 1-8 optionally includes a control circuit configured to recurrently initiate an impedance measurement, and recurrently calculate the second supply voltage using the measured impedance.

In Example 10, the subject matter of Example 9 optionally includes a control circuit configured to initiate an impedance measurement when delivery of the load current is enabled.

In Example 11, the subject matter of one or any combination of Examples 1-10 optionally includes a supply voltage generating circuit having a supply capacitor configured to provide a supply voltage to the therapy circuit, a voltage reference circuit configured to provide a changeable reference voltage value, and a voltage converter circuit, communicatively coupled to the storage capacitor and the voltage reference circuit, configured to provide energy to the storage capacitor according to the reference voltage value. The control circuit is optionally configured to initiate adjustment of the supply voltage of the storage capacitor from the first supply voltage value to the second supply voltage value by changing the reference voltage value.

Example 12 can include subject matter (such as a method, a means for performing acts, or a machine-readable medium including instructions that, when performed by the machine, cause the machine to perform acts), or can optionally be combined with the subject matter of one or any combination of Examples 1-11 to include such subject matter, comprising applying a first supply voltage value to a neural stimulation therapy circuit of an ambulatory medical device when the ambulatory medical device is in a first mode and, upon exiting the first mode, measuring (by the ambulatory medical device) an impedance at an output of the therapy circuit, determining a second supply voltage value sufficient for the therapy circuit to provide a specified load current value to the measured impedance, and applying the second supply voltage value to the neural stimulation therapy circuit. Such subject matter can include means for applying a first supply voltage value to a neural stimulation therapy circuit of an ambulatory medical device when the ambulatory medical device is in a first mode, illustrative examples of which include a supply voltage generating circuit and a voltage converter circuit. Such subject matter can include means for measuring an impedance at an output of the therapy circuit, an illustrative example of which includes an impedance measuring circuit that applies one of a known current or voltage and measures the resulting voltage or current to determine the impedance. Such subject matter can include means for determining a second supply voltage value sufficient for the therapy circuit to provide a specified load current value to the measured impedance, illustrative examples of which include a control circuit, a voltage compliance monitor circuit, and a current measurement circuit. Such subject matter can include means for applying the second supply voltage value to the neural stimulation therapy circuit, illustrative examples of which include a supply voltage generating circuit and a voltage converter circuit.

In Example 13, the subject matter of Example 12 optionally includes a specified current value that is a programmable therapy current value, and applying the second supply voltage value includes re-determining the second supply voltage value when the programmable therapy current value is changed.

In Example 14, the subject matter of one or any combination of Examples 12 and 13 optionally include monitoring operation of the therapy circuit to detect whether the second supply voltage value is at least equal to a minimum voltage necessary to operate the therapy circuit and provide the specified load current value to the measured impedance, and incrementally increasing the second supply voltage value when determining that the second supply voltage value is less than the minimum voltage.

In Example 15, the subject matter of Example 14 optionally includes incrementally decreasing the second supply voltage value when determining that the second supply voltage value is greater than the minimum voltage.

In Example 16, the subject matter of one or any combination of Examples 12-15 optionally includes recurrently measuring the impedance at the output of the therapy circuit, recurrently calculating the minimum voltage necessary to operate the therapy circuit and provide the specified load current value to the measured impedance, and adjusting the second supply voltage value to be at least equal to the calculated minimum voltage.

In Example 17, the subject matter of one or any combination of Examples 12-16 optionally includes monitoring operation of the therapy circuit to detect whether a delivered load current value is less than the specified load current value, and adjusting the second supply voltage to adjust the delivered load current value toward a specified target load current value.

In Example 18, the subject matter of one or any combination of Examples 12-17 optionally includes recurrently measuring the impedance over a specified time duration to obtain a range of impedance values, and wherein the second supply voltage value is calculated using the maximum impedance value obtained.

In Example 19, the subject matter of one or any combination of Examples 12-18 optionally includes recurrently measuring the impedance, and recurrently calculating the second supply voltage using the measured impedance.

In Example 20, the subject matter of one or any combination of Examples 12-19 optionally includes generating an alert by the ambulatory medical device when the ambulatory medical device is unable to generate a second supply voltage value that is sufficient to provide the specified load current value to the measured impedance.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation of combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An ambulatory medical device comprising:
    a therapy circuit configured to provide a specified neural stimulation current value at an output of the therapy circuit;
    an impedance measurement circuit configured to measure a value of impedance at the output of the therapy circuit;
    a supply voltage generating circuit configured to provide an adjustable supply voltage value to the therapy circuit including a first supply voltage value when in a first mode;
    a control circuit communicatively coupled to the therapy circuit, the impedance measuring circuit, and the supply voltage generating circuit, wherein the control circuit, upon receiving an indication to exit the first mode, is configured to:
        initiate an impedance measurement by the impedance measurement circuit;
        determine a second supply voltage value using the impedance measurement and the specified neural stimulation current value, wherein the second supply voltage value is sufficient to operate the therapy circuit and to provide the specified neural stimulation current value to the measured impedance; and
        initiate a change from the first supply voltage value to the second supply voltage value.

2. The device of claim 1,
    wherein the therapy circuit includes a programmable current circuit configured to provide a programmable load current value to the output of the therapy circuit; and
    wherein the control circuit is configured to re-determine the second supply voltage value when the programmable load current value is changed.

3. The device of claim 1, including:
    a voltage compliance monitor circuit configured to detect when the second supply voltage value is less than the minimum voltage necessary to operate the therapy circuit and provide the specified load current value to the measured impedance; and
    wherein the control circuit is configured to incrementally increase the second supply voltage value when the second supply voltage value is less than the minimum voltage.

4. The device of claim 3,
    wherein the voltage compliance monitor circuit is configured to detect when the second supply voltage value is greater than the minimum voltage necessary to operate the therapy circuit and provide the specified load current value to the measured impedance; and wherein the control circuit is configured to incrementally decrease the second supply voltage value when the second supply voltage value is greater than the minimum voltage.

5. The device of claim 1, wherein the control circuit is configured to:

recurrently initiate an impedance measurement;

recurrently calculate the minimum voltage necessary to operate the therapy circuit and provide the specified load current value to the measured impedance; and adjust the second supply voltage to be at least equal to the calculated minimum voltage.

6. The device of claim 1, including:

a current measuring circuit communicatively coupled to the output of the therapy circuit and configured to detect whether a delivered load current value is less than the specified load current value; and wherein the control circuit is configured to incrementally increase the second supply voltage when determining that the delivered load current value is less than the specified load current value.

7. The device of claim 6, wherein the current measuring circuit includes a sense resistor in series with a port configured for electrical connection to the load; and wherein the current measuring circuit is configured to measure a voltage across the sense resistor to detect whether the delivered load current value is less than the specified load current value.

8. The device of claim 1, wherein the control circuit is configured to:

recurrently initiate an impedance measurement during a specified time duration to obtain a range of impedance values;

determine a maximum impedance value using the obtained range of impedance values and calculate the minimum voltage using the maximum impedance value of the obtained range of impedance values.

9. The device of claim 1, wherein the control circuit is configured to:

recurrently initiate an impedance measurement; and recurrently calculate the second supply voltage using the measured impedance.

10. The device of claim 9, wherein the control circuit is configured to initiate an impedance measurement when delivery of the load current is enabled.

11. The device of claim 1, wherein the supply voltage generating circuit includes:

a supply capacitor configured to provide a supply voltage to the therapy circuit;

a voltage reference circuit configured to provide a changeable reference voltage value; and a voltage converter circuit, communicatively coupled to the storage capacitor and the voltage reference circuit, configured to provide energy to the storage capacitor according to the reference voltage value, wherein the control circuit is configured to initiate adjustment of the supply voltage of the storage capacitor from the first supply voltage value to the second supply voltage value by changing the reference voltage value.

12. A method comprising:

applying a first supply voltage value to a neural stimulation therapy circuit of an ambulatory medical device when the ambulatory medical device is in a first mode; and upon exiting the first mode:

measuring, by the ambulatory medical device, an impedance at an output of the therapy circuit calculating, by the ambulatory medical device, a second supply voltage value using measured impedance and a specified neural stimulation current value, wherein the second supply voltage value is sufficient for the therapy circuit to provide the specified neural stimulation current value to the measured impedance; and applying the second supply voltage value to the neural stimulation therapy circuit.

13. The method of claim 12, wherein the specified current value is a programmable therapy current value, and wherein applying the second supply voltage value includes re-determining the second supply voltage value when the programmable therapy current value is changed.

14. The method of claim 12, including:

monitoring operation of the therapy circuit to detect whether second supply voltage value is at least equal to a minimum voltage necessary to operate the therapy circuit and provide the specified load current value to the measured impedance; and incrementally increasing the second supply voltage value when determining that second supply voltage value is less than the minimum voltage.

15. The method of claim 14, including incrementally decreasing the second supply voltage value when determining that the second supply voltage value is greater than the minimum voltage.

16. The method of claim 12, including:

recurrently measuring the impedance at the output of the therapy circuit;

recurrently calculating the minimum voltage necessary to operate the therapy circuit and provide the specified load current value to the measured impedance; and adjusting the second supply voltage value to be at least equal to the calculated minimum voltage 17. The method of claim 12, including:

monitoring operation of the therapy circuit to detect whether a delivered load current value is less than the specified load current value; and adjusting the second supply voltage to adjust the delivered load current value toward a specified target load current value.

18. The method of claim 12, wherein measuring an impedance at an output of the therapy circuit includes recurrently measuring the impedance over a specified time duration to obtain a range of impedance values and determining a maximum impedance value using the obtained range of impedance values, and wherein the second supply voltage value is calculated using the maximum impedance value obtained.

19. The method of claim 12, wherein measuring an impedance at an output of the therapy circuit includes recurrently measuring the impedance, and wherein applying the second supply voltage value includes recurrently calculating the second supply voltage using the measured impedance.

20. The method of claim 12, including generating an alert by the ambulatory medical device when the ambulatory medical device is unable to generate a second supply voltage value that is sufficient to provide the specified load current value to the measured impedance.

* * * * *